United States Patent [19]

Nissfolk et al.

[11] Patent Number: 5,767,334

[45] Date of Patent: Jun. 16, 1998

[54] METHOD FOR REMOVING CATALYST FROM AN OLIGOMER PRODUCT

[75] Inventors: Fredrik Nissfolk, Borga; Raimo Linnaila, Porvoo, both of Finland; Ivo Smeets, Hasselt, Belgium; Vesa-Matti Lehtinen; Kauno Alastalo, both of Porvoo, Finland; Filip Thierie, Borgloon, Belgium

[73] Assignee: Neste Alfa Oy, Espoo, Finland

[21] Appl. No.: 602,736

[22] PCT Filed: Jun. 23, 1995

[86] PCT No.: PCT/BE95/00061

§ 371 Date: Apr. 8, 1996

§ 102(e) Date: Apr. 8, 1996

[87] PCT Pub. No.: WO96/00201

PCT Pub. Date: Jan. 4, 1996

[30] Foreign Application Priority Data

Jun. 24, 1994 [EP] European Pat. Off. ............. 94870107

[51] Int. Cl.⁶ .................. C07C 2/08; C07C 7/04
[52] U.S. Cl. ................ 585/525; 585/521; 585/800
[58] Field of Search ................ 585/504, 520, 585/521, 525, 800, 809; 203/91, 2

[56] References Cited

U.S. PATENT DOCUMENTS

| | | | |
|---|---|---|---|
| 2,588,358 | 3/1952 | Carlson et al. | 585/521 |
| 4,239,930 | 12/1980 | Allphin | 585/517 |
| 4,263,467 | 4/1981 | Madgavkar | 585/525 |
| 4,956,512 | 9/1990 | Nissfolk et al. | 585/521 |
| 5,254,784 | 10/1993 | Nurminen et al. | 585/525 |

FOREIGN PATENT DOCUMENTS

| | | |
|---|---|---|
| 0318186 | 5/1989 | European Pat. Off. |
| 0349277 | 1/1990 | European Pat. Off. |
| 0364815 | 4/1990 | European Pat. Off. |
| 0364889 | 4/1990 | European Pat. Off. |
| 0493024 | 7/1992 | European Pat. Off. |

*Primary Examiner*—Glenn Caldarola
*Assistant Examiner*—Thuan D. Dang
*Attorney, Agent, or Firm*—Watson Cole Grindle Watson, P.L.L.C.

[57] ABSTRACT

A method for removing catalyst from an olefinic oligomerization product includes the steps of oligomerizing one or more olefins in the presence of a $BF_3$ cocatalyst complex, and distilling the oligomerization product while separating vaporized $BF_3$ cocatalyst complex, the distillation step including, simultaneously to the separation of $BF_3$ cocatalyst complex, a separation of vaporized unreacted monomer from a bottom product which becomes substantially free from $BF_3$ cocatalyst complex.

19 Claims, 1 Drawing Sheet

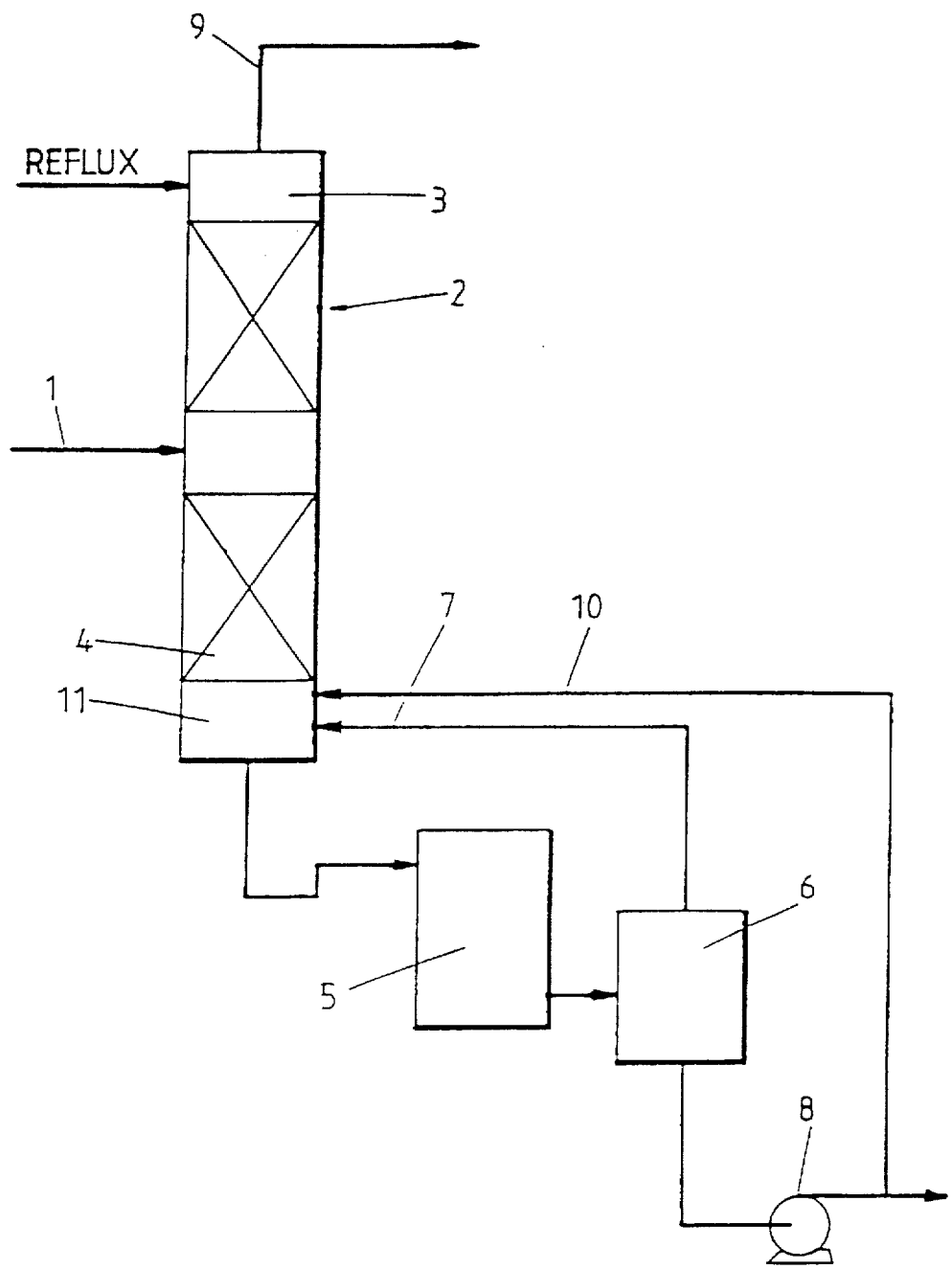

METHOD FOR REMOVING CATALYST FROM AN OLIGOMER PRODUCT

BACKGROUND OF THE INVENTION

1. Field of the Invention

The present invention relates to a method for removing catalyst from an olefinic oligomerization product which includes the steps of oligomerizing one or more olefins in the presence of a $BF_3$ cocatalyst complex and distilling the oligomerization product while separating vaporized $BF_3$ cocatalyst complex.

2. The Prior Art

Poly-α-olefin type base oils are widely used in high quality lubricants. The most preferred starting material for the poly-α-olefin base oils is 1-decene, which yields a product with excellent viscosity-volatility relationships and high viscosity indices. Such oligomer-derived base oils are especially adapted for use under rigorous conditions and are particularly suitable for general use in an arctic environment. Other olefins are also usually used in oligomerization processes, for example straight or branched $C_4$–$C_{20}$ olefin, advantageously a $C_6$–$C_{12}$ olefin-1.

The use of promoted borontrifluoride gives good control of the oligomerization process and furthermore a good conversion of monomer to desired poly-α-olefin base oils. Borontrifluoride alone is not an active catalyst; it requires a promoter in order to perform as an oligomerization catalyst. The promoter or cocatalyst can be water, alcohol, acid, ether, ketone or mixtures of these. The choice of cocatalyst has a significant impact on the oligomerization. Most commonly alcohols as n-propanol and n-butanol are used. Other cocatalysts may also be used as for example $C_1$–$C_{15}$ alcohols, advantageously a $C_1$–$C_{10}$ alcohol, a polyol or $C_1$–$C_7$ carboxylic acids.

$BF_3$ forms complexes with the cocatalysts. The activity and performance of the $BF_3$-complexes as oligomerization catalysts are improved by supplying $BF_3$ in excess to what is needed for formation of the catalyst complex. Excess $BF_3$ is supplied by either bubbling $BF_3$-gas through the reaction mixture or by carrying out the reaction under $BF_3$-pressure.

The $BF_3$-cocatalyst complex is either formed in situ in the oligomerization process or it is prepared by contacting $BF_3$ and cocatalyst prior to introduction to the process.

For those skilled in the art it is obvious that the oligomerization can be carried out in various types of reactor systems where the free $BF_3$, the catalyst complex and the monomer are brought together. In general the catalyst complexes are not very well soluble in either the monomer or the oligomers formed in the process. Good contact between the three phases is essential in order to achieve an efficient oligomerization process. The oligomerization reaction, as well as the formation of $BF_3$-cocatalyst complex, are exothermic reactions, and in order to enable a controlled oligomerization path, the oligomerization system has to be equipped with an adequate cooling system.

Various kinds of reactor systems are known in the prior art for use in oligomerization by liquid phase catalyst complexes e.g., stirred tank reactors operated either in batch or continuous mode, loop reactors, tubular reactors or combinations of the latter. For operation in continuous mode the process can also be carried out in two or more serial-connected reactors. Fixed bed reactors may be used when the catalyst complex is present as a solid.

The oligomerization reactor product consists of unreacted monomer, dimers, trimers and higher oligomers, free and dissolved $BF_3$ and catalyst complex.

Due to the toxicity and corrosion risks, the catalyst complex and free $BF_3$ have to be carefully removed from the oligomer product. Especially fluor compounds are harmful for the generally used nickel-based catalyst used for hydrogenating the final products.

Removal of the $BF_3$ catalyst can be achieved by washing the reactor product with caustic water solution or ammonia water solutions. The alkaline wash is generally followed by aqueous wash in one or more steps to achieve a sufficiently clean oligomer mixture for further processing.

When a catalyst recovery is applied e.g., by water extraction of $BF_3$ (EP-A-0349277 and EP-A-0364815), or by gravitational separation (EP-A-0364889 or U.S. Pat. No. 4,239,930), there is still a need to subject the oligomer product to additional washing steps.

A catalyst recovery comprising a vacuum distillation procedure of the oligomerization product and a step of recycling the vaporized $BF_3$ cocatalyst complex is disclosed in EP-A-0318186. However this procedure still needs a washing with an alkaline solution and the bottom product contains a part of the monomer fraction of the oligomerization product.

Applying alkaline and aqueous washing generates quantitative amounts of waste water containing various fluor and boron salts, which for environmental reasons have to be treated in a proper way. The disposal of this type of waste water is costly. Another disadvantage of the oligomer washing is a possible formation of oligomer-water emulsions, which cause operational problems for the washing process. In worst case situations the emulsion formation may cause loss of product. Furthermore, the washed product tends to contain dissolved water, which may have to be removed by drying processes before the product can be further treated. Especially if oligomer separation by vacuum distillation is carried out subsequent to the washing process, any water present in the distillation feed will cause disturbances in the distillation.

Accordingly, the object of present invention is to provide a process for recovering the $BF_3$-cocatalyst complex and to achieve efficient removal of $BF_3$-cocatalyst traces from the oligomer product without subjecting the oligomeric product to any kind of aqueous washing. Another object of the present invention is to separate during the recovery the $BF_3$-cocatalyst complex, free and dissolved $BF_3$ and unreacted monomer, in order to obtain an oligomer product consisting of dimer, trimer, tetramer and heavier oligomers essentially free of $BF_3$-residues.

SUMMARY OF THE INVENTION

According to the invention the oligomer product is fed into a distillation column operating at low pressure and wherein its top is maintained at a temperature higher than the boiling temperature of the unreacted monomer and the cocatalyst complex and lower than the decomposition temperature of the cocatalyst complex at the applied pressure, while its bottom is maintained at temperature higher than the boiling temperature of the unreacted monomer and the cocatalyst complex and lower than the dimer fraction at the applied pressures, such that substantially dimer-free distillate containing vaporized $BF_3$ cocatalyst complex and vaporized unreacted monomer will be formed at the top of the distillation column and a condensate will be formed at the bottom of the distillate column which will contain dimers, trimers and higher oligomers and be substantially free of $BF_3$ cocatalyst complex and unreacted monomer. Depending on the monomer oligomerized, the conditions in the distillation column are selected in order that all BF$_3$-residues are vaporized from the bottom product and preferably also all unreacted monomer. In these conditions, no washing step of the oligomerization product is necessary. Remarkable savings are achieved in the total catalyst consumption and in the expenses incurred in removing residues.

BRIEF DESCRIPTION OF THE FIGURE

The invention will now be described more in detail with the aid of a non limitative example and with reference to the FIGURE which represents a flow diagram of the vacuum distillation step according to the invention.

DETAILED DESCRIPTION OF THE PREFERRED EMBODIMENT

In this example the oligomerization is carried out in a continuous stirred tank reactor, which is continuously charged with fresh and recycled monomer and with recycled catalyst complex and which is pressurized with BF$_3$ in order to establish an excess of BF$_3$. Cooling is provided by circulating the reactor content via an external heat-exchanger. For example 1-decene is used as monomer and n-butanol as cocatalyst. The temperature is set on −10° C. to +70° C., preferably on 0° to 50° C., for example on 30° C. BF$_3$ gas is supplied at constant rate to obtain the quantity required in producing BF$_3$-BuOH complex. The pressure is maintained to 0.05 to 10 bars, preferably to 1.5 to 4 bars.

Subsequent to oligomerization the reactor product, consisting of unreacted monomer, dimers, trimers and higher oligomers, free and dissolved BF$_3$ and catalyst complex, is fed in 1 to a distillation column 2 operated under vacuum. Pressure at the top 3 of the column is lower than 30 mbar, preferably lower than 15 mbar, for example 10 mbar. The temperature is maintained as low as possible in the upper part of the column, which is located above the feed position 1, for example 50°–60° C. In any case at the top 3 of the column the temperature is less than 70° C., preferably 45°–50° C. Above 70°–80° C., the catalyst complex of the present example starts to decompose into undesired products. Preferably, the temperature at the top 3 of the column 2 is also lower than the boiling temperature of the dimer fraction resulting from the oligomerization, in order to avoid a distillation of any dimer. Vaporization of the catalyst complex and unreacted monomer at low temperature is achieved while operating at the above disclosed low pressures.

In order to obtain an essentially complete removal of both unreacted monomer and BF$_3$-residues from the bottom product, the pressure at the lower packing 4 of the column is maintained lower than 50 mbar, preferably lower than 25 mbar. Here, the temperature is lower than the boiling temperature of the dimer fraction, and lower than the decomposition temperature of the cocatalyst complex, at the applied pressures, and higher than the boiling temperature of the unreacted monomer and of the cocatalyst complex.

In the present example, at the lower packing 4 of the column, a temperature of 70°–80° C. is maintained at pressure of 15 mbar.

In the illustrated example, a reboiler 5 is mounted to receive the bottom product of the column 2 and to heat the latter. This product is completely free of cocatalyst complex and of monomer. In a following flash drum 6 a portion of vaporized dimer is separated from the heated oligomerized product at a temperature of for example 200°–220° C. and the vaporized dimer portion is recycled in 7 into the bottom 11 of the distillation column.

By means of a pump 8, the product issuing from the bottom of the flash drum 6 and consisting of the desired products (dimers, trimers, tetramers and heavier oligomers) essentially free from monomer and BF$_3$-residues is transferred towards the next treatment.

At the outlet of the pump 8, bottom product still at its boiling point is recycled via a minimum-flow line 10 into the bottom 11 of the distillation column.

In the illustrated example the bottom 11 of the distillation column is consequently a contact zone for a liquid coming down from the lower packing 4, a dimer vapor rising from the flash drum 6 and a bottom product at its boiling point issuing from the outlet of the pump 8. If residual monomer and catalyst complex are still included in the liquid from the lower packing 4, they are evaporated in the bottom 11 of the column by the heat inputs via lines 7 and 10.

In this way, by a direct heating, it is possible to prevent especially the catalyst complex from entering the reboiler 5, where catalyst residues can cause severe corrosion. The evaporation of said components is advantageously achieved without exposing the catalyst complex to hot heat-transfer surfaces. Obviously the step of heating the bottom product in the bottom 11 of the column could be obtained also by other means, for example by heat exchangers.

Obviously the introduction in 7 of the vaporized dimer and in 10 of a fraction of vaporized bottom product may be controlled by any known means. This introduction must regulate the required heat for monomer and catalyst complex evaporation and enable a good temperature control of the bottom 11 of the column. In the bottom 11 of the column, at a pressure of approximately 15 mbar, the temperature is in the present example regulated advantageously to a temperature of 130°–150° C.

The distillate fraction leaving in 9 the distillation column 2 consists of free BF$_3$, catalyst complex and monomer. Distillate vapor is condensed and catalyst complex is separated from the monomer phase by gravitation and the two are independently recycled back to the oligomerization process. Uncondensable BF$_3$-gas is optionally trapped in a vacuum system such as the system disclosed in EP-A-0493024. The catalyst complex formed in the vacuum system as a result of the reaction between BF$_3$ and n-butanol is also recycled to the oligomerization process.

It is also possible to conceive a direct recycling of the condensed distillate without previous separation of the monomer from the cocatalyst complex. A separation of the condensed vapour may also be carried out for example by means of a centrifuge or cyclonesystem.

We claim:

1. Method for removing catalyst from an olefinic oligomerization product, comprising the steps of:

oligomerizing one or more olefins in the presence of a BF$_3$ cocatalyst complex in order to obtain an oligomerization product containing unreacted monomer, dimers, trimers, higher oligomers and BF$_3$ cocatalyst complex, distilling at low pressure and temperature said oligomerization product by feeding said oligomerization product into a distillation column between a top and a bottom thereof, wherein the distillation comprises:

maintaining at the top of said distillation column a temperature higher than the boiling temperature of the unreacted monomer and of the cocatalyst complex and lower than the decomposition temperature of said cocatalyst complex at the applied pressure, and removing from the top of the column a distillate which contains vaporized BF$_3$ cocatalyst complex and vaporized unreacted monomer and which is substantially dimer-free, maintaining in a portion of said distillation column, which is located below where said feeding occurs, a temperature higher than the boiling temperature of the unreacted monomer and of the BF$_3$ cocatalyst complex and lower than the boiling temperature of the dimer fraction at the applied pressure, with formation of a bottom product which contains said dimers, trimers and higher oligomers and which is substantially free from BF$_3$ cocatalyst complex and from monomer, heating said bottom product within the bottom of the column in order to evaporate optionally residual unreacted monomer and BF$_3$ cocatalyst complex, and removing from the bottom of the column a heated bottom product which is substantially free from BF$_3$ cocatalyst complex and from monomer.

2. Method according to claim 1, comprising the steps of condensing the distillate and of isolating the condensed BF$_3$ cocatalyst complex from the condensed monomer.

3. Method according to claim 2, wherein the condensed BF$_3$ cocatalyst complex is isolated from the condensed monomer by gravitation or centrifugation.

4. Method according to claim 2, wherein during said step of condensing, uncondensable BF$_3$-gas is trapped in a vacuum system wherein trapped BF$_3$ and cocatalyst are reacted to form BF$_3$ cocatalyst complex.

5. Method according to claim 2, comprising a step of recycling BF$_3$ cocatalyst complex resulting from said step of isolating and/or isolated monomer back to the oligomerization.

6. Method according to claim 1, comprising the steps of condensing the distillated product and of recycling a so condensed mixture back to the oligomerization.

7. Method according to claim 1, wherein the olefin to oligomerize is a straight or branched $C_1$–$C_{20}$ olefin.

8. Method according to claim 1, wherein the cocatalyst is a $C_1$–$C_{15}$ alcohol or a polyol or a $C_1$–$C_7$ carboxylic acid, advantageously a $C_1$–$C_{10}$ alcohol.

9. Method according to claim 1, wherein the pressure is lower than 30 mbar.

10. Method according to claim 1, wherein the temperature at the top of the distillation column is lower than 70° C., at a pressure of approximately 10 mbar.

11. Method according to claim 1, wherein the temperature in said portion of the distillation column is equal or lower than 80° C., at a pressure of approximately 15 mbar.

12. Method according to claim 1, wherein the temperature in the bottom of the column is of 130°–150° C. at a pressure of approximately 15 mbar.

13. Method according to claim 1, wherein said step of heating comprises an introduction into the bottom of the column of at least one vaporized portion of the bottom product issuing from the distillation column.

14. Method according to claim 1, comprising the steps of heating the bottom product of the distillation column in a reboiler, of separating vaporized dimer from the heated bottom product and of recycling said vaporized dimer into the bottom of the distillation column.

15. Method according to claim 14, comprising the steps of pumping the heated bottom product from which vaporized dimer was separated and thereafter of recycling a vaporized portion of said pumped bottom product into the bottom of the distillation column.

16. Method according to claim 1, wherein the olefin to oligomerize is a straight or branched $C_6$–$C_{12}$ olefin-1.

17. Method according to claim 4, comprising a step of recycling BF$_3$ cocatalyst complex resulting from said reaction between trapped BF$_3$ and cocatalyst, and/or isolated monomer back to the oligomerization.

18. A method for removing BF$_3$ cocatalyst complex from an olefinic oligomerization product comprising unreacted monomer, dimers, trimers, higher oligomers, and BF$_3$ cocatalyst complex comprising the steps of:

providing a distillation column having a top end and a bottom end, feeding said olefinic oligomerization product to said distillation column between said top end and said bottom end, maintaining the top end of said distillation column at a temperature higher than a boiling temperature of said unreacted monomer and said BF$_3$ cocatalyst complex but lower than a decomposition temperature of said BF$_3$ cocatalyst complex, maintaining a portion of said distillation column which is located below where said feeding occurs at a temperature higher than a boiling temperature of said unreacted monomer and said BF$_3$ cocatalyst complex and lower than a boiling temperature of said dimers, such that vaporized BF$_3$ cocatalyst complex and vaporized unreacted monomer rise to said top end and form a substantially dimer-free vaporized fraction, and said dimers, trimers and higher oligomers fall to said bottom end and form a bottom product fraction substantially free of BF$_3$ cocatalyst complex and unreacted monomer, heating said bottom product within the bottom end of the column in order to evaporate optionally residual unreacted monomer and BF$_3$ cocatalyst complex, and removing from the bottom end of the column a heated bottom product which is free from BF$_3$ cocatalyst complex and from monomer and which does not necessitate any sodium hydroxide washing step.

19. A method according to claim 18, wherein the temperature at the top end of the distillation column is maintained at 45° to 70° C. at a pressure of 10–30 mbar, and the bottom end of the distillation column is heated at a temperature of 130° to 150° C. at a pressure of about 15 mbar.

* * * * *